United States Patent
King

(10) Patent No.: US 7,594,520 B2
(45) Date of Patent: Sep. 29, 2009

(54) METHOD OF MAKING A DUAL FILTER

(75) Inventor: Joseph A. King, Wayzata, MN (US)

(73) Assignee: King Technology, Hopkins, MN (US)

( * ) Notice: Subject to any disclaimer, the term of this patent is extended or adjusted under 35 U.S.C. 154(b) by 0 days.

(21) Appl. No.: 11/983,897

(22) Filed: Nov. 13, 2007

(65) Prior Publication Data

US 2008/0087598 A1   Apr. 17, 2008

Related U.S. Application Data

(60) Division of application No. 11/044,480, filed on Jan. 27, 2005, now Pat. No. 7,335,299, which is a division of application No. 10/093,651, filed on Mar. 11, 2002, now Pat. No. 7,168,574, which is a continuation-in-part of application No. 09/550,668, filed on Apr. 17, 2000, now Pat. No. 6,446,814.

(60) Provisional application No. 60/130,468, filed on Apr. 22, 1999.

(51) Int. Cl.
*D03D 49/02* (2006.01)

(52) U.S. Cl. ..................................... 139/1 R

(58) Field of Classification Search .............. 210/198.1, 210/205, 206, 263, 282, 283, 284, 290, 291, 210/169; 139/1 R
See application file for complete search history.

(56) References Cited

U.S. PATENT DOCUMENTS

| | | | | | |
|---|---|---|---|---|---|
| 3,872,013 | A | * | 3/1975 | Nishino et al. | 210/317 |
| 3,930,000 | A | * | 12/1975 | Margraf | 514/184 |
| 4,071,636 | A | * | 1/1978 | Nishino et al. | 427/244 |
| 4,601,460 | A | * | 7/1986 | Tyler et al. | 266/216 |
| 4,772,395 | A | * | 9/1988 | Tungatt et al. | 210/506 |
| 5,004,648 | A | * | 4/1991 | Hane et al. | 428/364 |
| 6,165,243 | A | * | 12/2000 | Kawaguchi et al. | 55/524 |

* cited by examiner

*Primary Examiner*—Chester T Barry
(74) *Attorney, Agent, or Firm*—Jacobson & Johnson LLC

(57) ABSTRACT

A dual filter apparatus and a process of making a dual filter apparatus that minimizes disruption to the normal flow pattern through the filter apparatus by forming a porous medium suitable to carry a fluid activator and placing an activator proximate the porous filter medium for in situ fluid treatment and removal of debris from the fluid by screening action of the porous filter medium that entraps debris thereon.

6 Claims, 13 Drawing Sheets

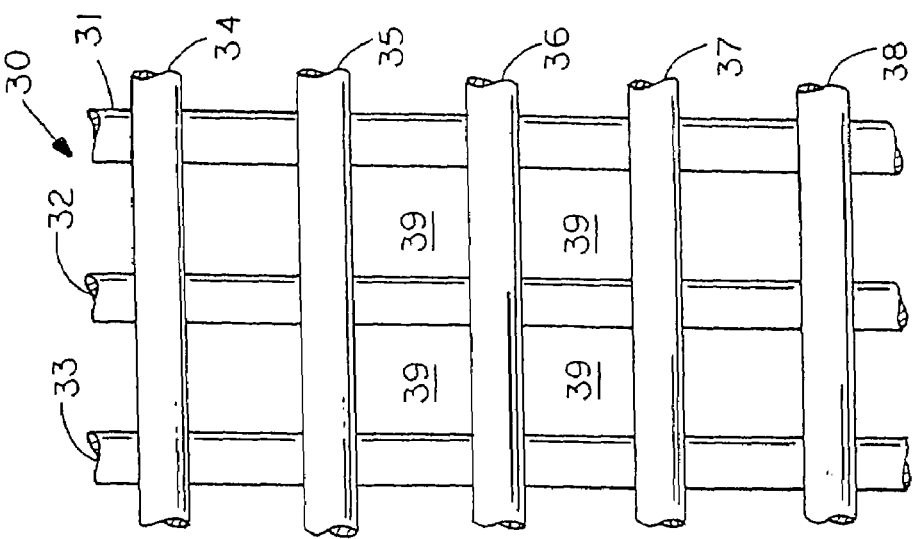
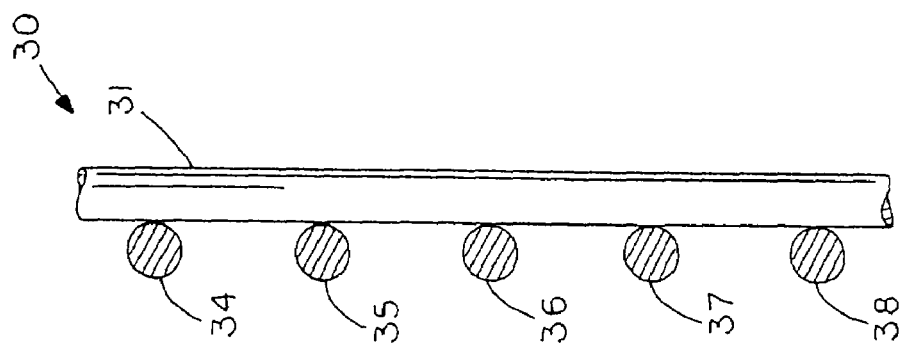
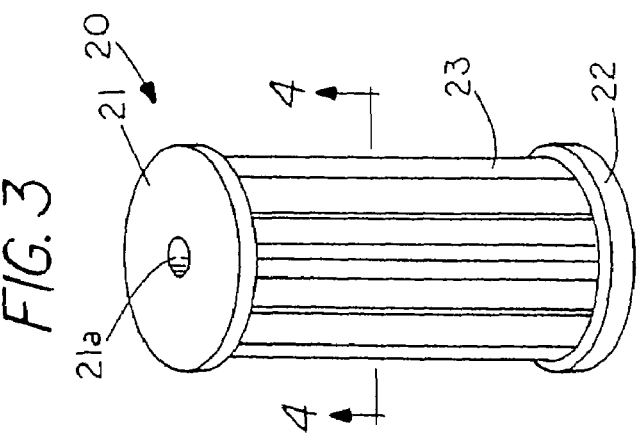
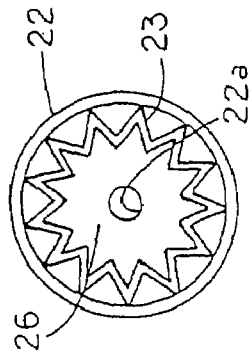

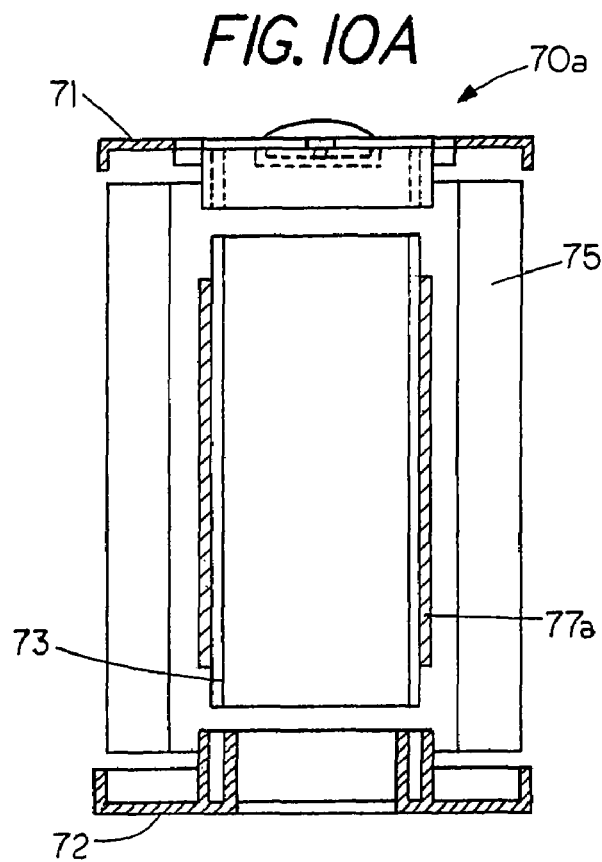
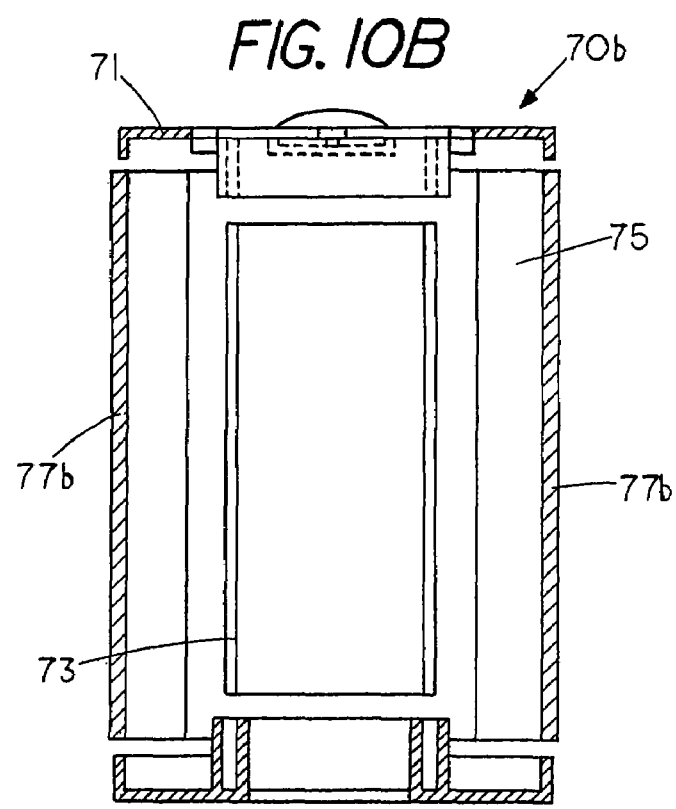

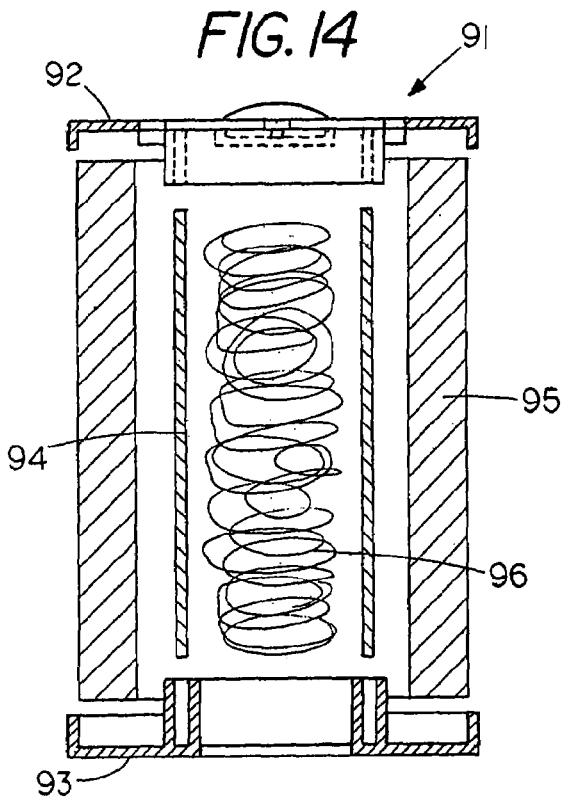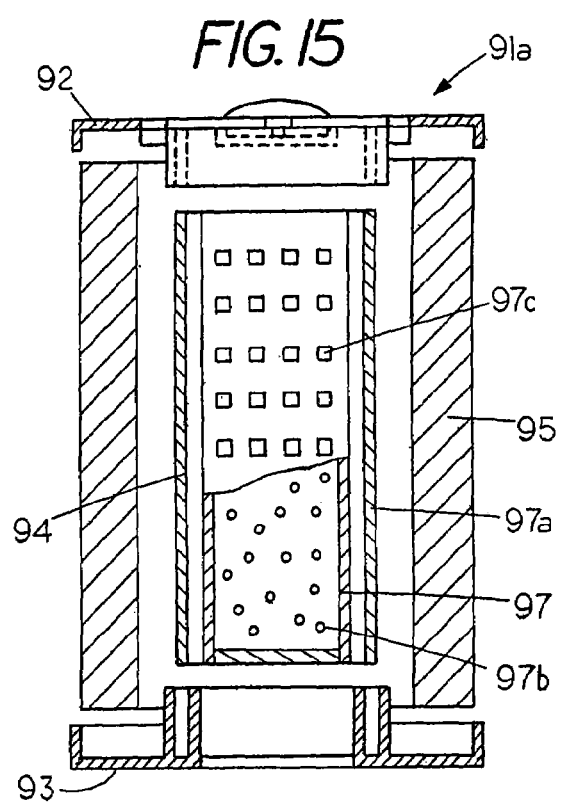

METHOD OF MAKING A DUAL FILTER

CROSS REFERENCE TO RELATED APPLICATIONS

This application is a division of application Ser. No. 11/044,480 filed Jan. 27, 2005, now U.S. Pat. No. 7,335,299 titled DUAL FILTER AND METHOD OF MAKING SAME (pending), which is a division of application Ser. No. 10/093,651 filed on Mar. 11, 2002, titled DUAL FILTER, now Pat. No. 7,168,574, which is a continuation-in-part of application Ser. No. 09/550,668, filed on Apr. 17, 2000, titled METHOD OF MAKING A DUAL FILTER, now Pat. No. 6,446,814 and parent provisional application No. 60/130,468, filed Apr. 22, 1999, titled DUAL FILTER AND METHOD OF MAKING.

FIELD OF THE INVENTION

This invention relates generally to a dual filter system and apparatus and, more specifically, to a filter carrying an activator to enable the filter to simultaneously and in situ treat the fluid as the fluid flows through the filter while minimizing disruption to the normal flow of fluid through the filter system.

BACKGROUND OF THE INVENTION

In water treatment systems it is known that activators such as bacteria killing materials comprising metal ions are effective in killing bacteria. One commonly used metal ion is the silver ion and another commonly used bacteria killing and material is the zinc ion. Other types of ions are used as algaecides. The difficulty in use of metal ions is to maintain the ion concentration within proper ranges since too low metal ion concentration results in ineffective killing of bacteria and to high metal ion concentrations can be harmful. Another difficulty is to be able to controllable release the materials to provide for water purification over an extended period of time.

It has been demonstrated that a single bacteria killing material that releases silver ions can be effectively used to kill bacteria in water systems such as spas, hot tubs and swimming pools over an extended period of time. In some cases multiple bacteria killing materials that releases both ions of silver and zinc are used to kill bacteria over an extended period of time.

In one embodiment of a bacteria killing material I use an adhesive that is securable to both a metal ion generating material and to a particle carrier that is placed in a container within the water supply. Water is allowed to flow through the container as the bacteria killing material controllable release metal ions to kill bacteria in the water. While the use of bacteria killing materials that release metal ions is known, the present invention is directed to the structure and mechanism for holding the bacteria killing materials so as not to interfere with the release of the bacteria killing materials such as metal ions without disrupting the normal flow of water through the system.

In most recirculation systems such as for swimming pools, spas and hot tubs a filter is included that removes unwanted waste particles from the water. In one embodiment, which is shown in U.S. Pat. No. 4,780,197 a container is placed in the core of the filter. The container is filled with a bacteria-killing material such as chlorine or bromine. In this type of arrangement one can provide for removal of waste particles as well as killing of bacteria in the same part of the system. While this type of system brings the bacteria killing and water purification into the filter housing it does not provide for in situ killing of bacteria and removal of debris. However, more importantly, devices placed in the core of the filter create obstructions to normal flow through the fluid filter. The first obstruction to normal flow is the container itself that hold the bactericide and the second obstruction to normal flow is the materials that are placed in the container. In the present invention the obstruction to normal flow of water through the filter system is substantially eliminated as the bacteria killing material is either secured directly to the filter medium or to a portion of the filter where the flow area is generally the largest thereby allowing one to maintain the normal flow patterns of the filter mechanism.

In the present invention, a water treatment composition, for example, a water purification material, such as a bacteria killing material is secured to a replaceable filter that normally removes debris from the water. With the present invention the replaceable filter performs a dual in situ function in that the filter simultaneously removes debris and kills bacteria. Consequently, when the filter is replaced due to accumulation of debris thereon the bacteria killing material is replaced in the same operation thus minimizing the consumer maintenance in maintaining a water system in proper condition. Thus the present invention becomes consumer friendly as the need for maintenance of the system can be reduced.

In one embodiment of the dual filter apparatus of the present invention, a bacteria killing material is affixed directly to fibers that are formed into a filter medium with the fibers formed into a network for screening removal of debris from the water. As water is directed through the filter medium formed from the fibers containing the bacteria killing material the filter medium traps debris thereon, while the bacteria killing material kills bacteria thereon. In this embodiment the dual filter apparatus simultaneously accomplishes the in situ task of both filtering debris from the water and killing bacteria as the water passes through the filter. Other embodiments and refinement of the invention are described herein. The preferred embodiment is described in relation to a water purification material comprising a bacteria killing material and other water purification materials such as algaecides, clarifiers or pH adjusters can be used with the present invention.

SUMMARY OF THE INVENTION

Briefly, the present invention comprises an in situ fluid treatment system comprising a dual filter having a porous medium for removing debris and an activator retained proximate the porous medium for treating the fluid while minimizing obstruction to normal flow through the system as well as a process of making a water purification device by dispersibly securing a bacteria killing material proximate a filter medium for removing debris.

BRIEF DESCRIPTION OF THE DRAWINGS

FIG. 3 is a perspective view of a cartridge filter of the present invention;

FIG. 4 is a cross-sectional view of the filter of FIG. 1 taken along lines 4-4 of FIG. 3;

FIG. 5 is a side view of a portion of a filter medium without a bacteria-killing material thereon;

FIG. 6 is a front view of the portion of the filter medium of FIG. 5;

FIG. 10A is similar to FIG. 10 but with the annular carrier insert engaging the exterior surface of the core;

FIG. 10B is similar to FIG. 10 but with the annular carrier insert engaging the exterior surface of the cartridge;

FIG. 14 shows a partial cross-sectional view of a water filter cartridge having a steel-wool pad-like carrier located within the cartridge core;

FIG. 15 shows a cross-sectional view of a water filter cartridge having a solid core carrier located within the cartridge core;

DESCRIPTION OF THE PREFERRED EMBODIMENT

In the invention described herein, one forms an in situ water purification system comprising a water treatment composition and a filter medium suitable for inserting into a water supply to both kill bacteria therein and to screen debris from the water. In one embodiment the water treatment composition comprises a carrier and a metal ion yielding material, which is secured to a filter medium. Attached to the carrier is a bacteria killing material which, in the preferred embodiment, comprises silver chloride (AgCl) coating located thereon. The silver chloride particles are suspended in an adhesive matrix that adhesively secures the silver chloride particles proximate thereto in an ion yielding relationship. Another suitable metal ion yielding material suitable for use is zinc.

The bacteria killing material is preferably a metal ion yielding material although other materials could be used if the materials can be maintained in active mode over an extended period of time. An example of silver ion yielding material is silver chloride, which is described more fully in my co-pending application Ser. No. 08/957,265, filed Oct. 24, 1997, titled Water Treatment Composition. Silver chloride is a white powder that can be melted or cast like a metal, and is derived from heating a silver nitrate solution and adding hydrochloric acid or salt solution to produce a silver chloride solution, which is then boiled or filtered either in the dark or under a ruby red light to produce the silver chloride powder. In one embodiment of described process, the silver chloride while still in solution is combined with an adhesive to form an adhesive silver chloride solution. The adhesive and the silver chloride solution are then applied to a carrier such as a pellet. The adhesive is then cured to produce a pellet having a silver chloride coating adhesively adhered thereto with both the zinc and the silver chloride available for reacting with the chemicals within a bacteria cell to kill or damage the bacteria.

In a preferred embodiment of process, the silver chloride while still in solution is combined with an adhesive to form an adhesive silver chloride solution which is applied directly to a filter material for use in screening waste particles from a water source. The term adhesively secured herein is meant to include a surface attachment structure that does not prevent the bacteria killing materials from releasing the ions to kill unwanted bacteria.

Figure 1:
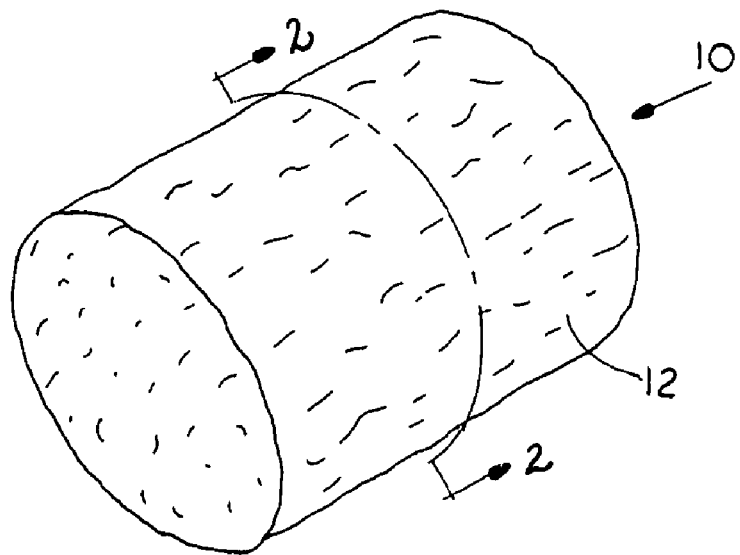
FIG. 1 is a perspective view of a carrier such as zinc pellet having a matrix carrying a silver yielding ion thereon.
Figure 2:
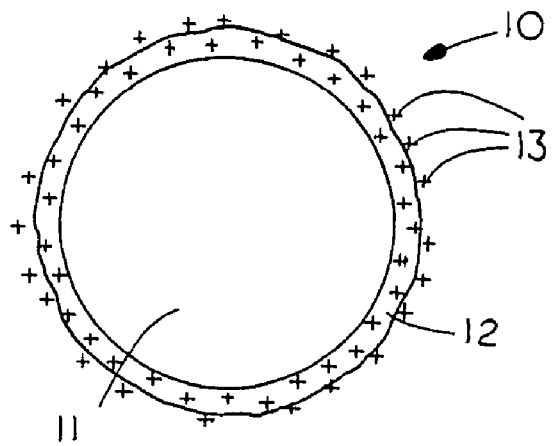
FIG. 2 is a sectional view taken along lines 2-2 of FIG. 1 to show the adhesive matrix located around the zinc pellet.

Referring to FIGS. 1 and 2, there is shown one way of forming a water treatment pellet 10 having an adhesive matrix coating 12. Adhesive matrix coating 12 comprises an adhesive that secures itself to the surface of both the silver ion generating material, which comprises silver chloride 13 and to the carrier, which is shown as a pellet 11. The process is described in relation to forming a silver chloride coating on a pellet so that the silver ion remains in a reactive state to react with the chemicals in the bacteria and effectively damage or kill the bacteria. However, the carrier 11 could be an active carrier, such as zinc as multiple ions generating material may be suitable for killing different types of bacteria.

FIG. 2 is a cross-sectional view of the silver chloride coated pellet 10 of FIG. 1 showing carrier particle 11 centrally located within adhesive matrix 12 that contains silver chloride 13 dispersed throughout the adhesive matrix 12. As can be seen from the drawing, the silver chloride 13 is maintained in the water porous matrix proximate the carrier pellet 11 to enable water to contact both the silver chloride located within the matrix. These types of pellets 11 can be placed directly into a container in the water to allow the bacteria killing materials to be released into the water. In one embodiment of the present invention the pellets containing the bacteria killing materials are secured directly to a filter medium so that the bacteria killing materials controllable release metal ions over an extended period of time.

In the embodiment shown in FIG. 2 one coats a carrier particle with a silver ion yielding material such as silver chloride by adhesively affixing or securing the silver chloride to the carrier through a non-soluble water porous adhesive matrix. A suitable material for adhesively securing the silver chloride proximate the carrier is commercially available gelatin which can be cross-linked with an aqueous solution of formaldehyde or glutaraldehyde to form a non-soluble, water penetrable matrix on the exterior surface of the carrier. Other suitable non-soluble water porous adhesive matrixes are polyvinyl acetate, polyurethane, epoxy resin, polyvinyl alcohol and polyvinyl acetate.

In the process of forming individual carriers for the ion generating materials, one forms a plurality of carriers or water treatment members typically an ⅛ inch or smaller which are suitable for inserting into an inline feeder. Instead of placing the individual carriers into a separate inline feeder the present invention includes the step of securing the carriers with the ion generating material directly to the filter material used to form a mechanical filter. In the preferred mode of the invention, the ion generating materials are secured directly to the fabric or filter medium without the use of a separate carrier. In both cases one obtains a dual filter system that provides for in situ killing of bacteria and removal of debris from the water flowing through the filter system.

The following examples illustrate how silver chloride particles were affixed proximate to the exterior surface of a carrier such as a pellet.

EXAMPLE 1

In order to coat a batch of pellets with an adhesive matrix containing silver chloride, 12.5 grams of silver nitrate are mixed in 25 ml of distilled water to form an aqueous silver nitrate mixture.

Next, 1.5 grams of gelatin are mixed in 25 ml of distilled water to form a gelatin mixture. The gelatin mixture is heated to a temperature of about 140 degrees F. To eliminate lumps in the gelatin mixture, the gelatin mixture is then strained through a screen. At this point, 5 grams of sodium chloride are mixed into the gelatin mixture. The gelatin mixture is then combined with the aqueous silver nitrate mixture to convert the silver nitrate into silver chloride to thereby form an aqueous silver chloride gelatin mixture. A batch of pellets having a maximum dimension of about ⅛ inch is then heated to about 140 degrees F. The pellets are then sprayed with the heated, aqueous silver chloride gelatin mixture. In order to form a matrix to affix the silver chloride to the pellets, the silver chloride gelatin mixture is then immersed in an aqueous bath of glutaraldehyde for about 12 hours to react the gelatin with the glutaraldehyde. The curing produce an adhesive matrix that secured the pellets with the silver chloride that is dispersed throughout the adhesive matrix. After curing, the pellets, which are covered with a coating of silver chloride, are rinsed and air dried to produce pellets with a silver chloride coating affixed proximate to the pellets.

EXAMPLE 2

The above process was repeated except instead of immersing the pellets with the silver chloride gelatin mixture in an aqueous bath of formaldehyde, the pellets with the silver chloride gelatin mixture were cured in an aqueous bath of formaldehyde.

In the above examples, the pellets had a maximum dimension of about ⅛ of an inch. Larger or smaller pellets could be used; however, for use as a water treatment composition in a dispensing valve, it is preferred to have carrier in multiple pellets in order to present a larger surface area to the water containing the bacteria. While securing of the bacteria killing material to the pellet carrier has been described the bacteria killing material can also be secured directly to the filter medium using the same adhesive.

In the above described method of forming the bacteria killing material, the adhesive used was gelatin as gelatin is capable of adhering to the surfaces of both the carrier and the silver chloride. That is, gelatin which can be cross-linked in the presence of formaldehyde or glutaraldehyde to obtain the necessary adhesive characteristics remains non-soluble in the water and unreactive with either the carrier or the silver chloride, and thus can hold the silver chloride proximate the carrier. That is the cross-linked gelatin not only forms a surface attachment but also forms a matrix to support or secure the silver chloride in proximity to the surface of the pellet. As the gelatin matrix is securable to the surfaces of both the silver chloride and to the pellets, one is assured that the silver ion yielding material will remain proximate each other to generate ions thereof. Also, the gelatin is desirable since the porosity of the adhesive matrix formed from gelatin allows bacteria containing water access to both the silver to enable both the silver ions to kill the bacteria in the water.

While gelatin is described as one of the adhesives, other suitable adhesives for securing the bacteria killing material to either the carrier or directly to the filter material so that the metal ions are controllable released include polyurethane, epoxy resin polyvinyl alcohol and polyvinyl acetate.

Referring to FIG. 3, reference numeral 20 identifies a dual filter apparatus of the present invention for simultaneously removing debris and killing bacteria. The filter 20, which is in cartridge form, includes a first end cap 21 and a second end cap 22 with a porous pleated filter medium 23 secured therebetween for screening waste particles from the water as the water flows through the filter medium 23. End cap 21 is shown with an opening 21a for ingress of fluid, and similarly FIG. 4 shows that end cap 22 includes an opening 22a for ingress of fluid into the interior 26 within the zigzag shaped filter medium 23.

FIG. 5 and FIG. 6 show a portion of one embodiment of a porous filter medium 30 that is arranged in a cross-hatched pattern to form a network comprised of a set of vertical fibers 31, 32 and 33 supporting a set of horizontal fibers 34, 35, 36, 37 and 38 to provide a plurality of regular openings 39 therein for screening waste particles of larger size from the water. In normal operation of the filter medium 30, water flows through the openings 39 while the large debris particles encounter the external network of fibers and is thus prevented from flowing through the filter medium 30. In time the filter becomes clogged with waste particles and needs to be replaced. In the embodiment of FIG. 5 and FIG. 6 the fibers are shown as round with regular shaped openings therein; however, it should be understood that the shape of the fibers, the shape of the openings as well as the use of non-fibers are suitable for making a filter for removing water carried debris as the water flows through the filter medium.

Figure 7:
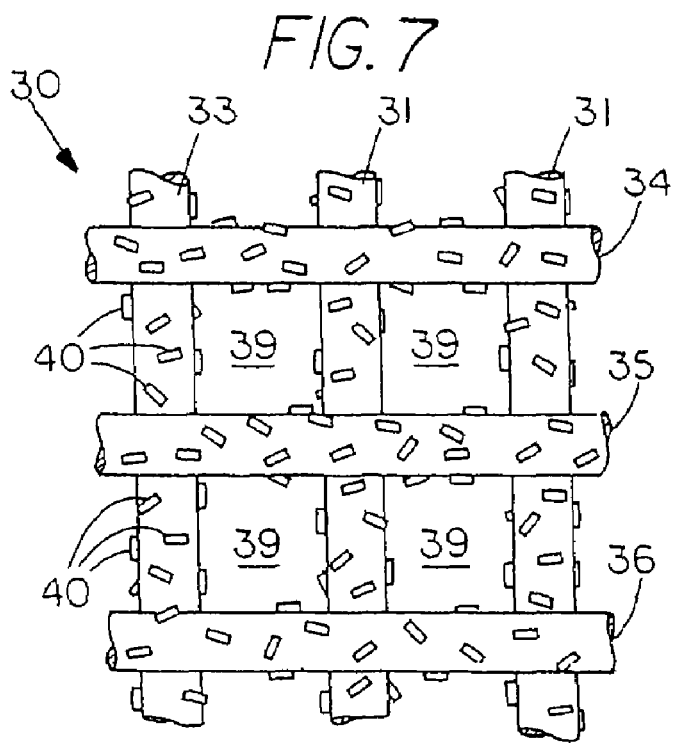
FIG. 7 is front view of a portion of the filter medium of FIG. 6 with a bacteria killing material secured thereto.

FIG. 7 shows the filter medium 30 with a water purification material such as a bacteria killing material 40 dispersibly secured to the surface of the filter medium so as to minimize obstruction to normal flow through the filter housing. In the embodiment shown, the bacteria killing material comprises silver chloride and a pellet acting as a carrier. By securing the bacteria killing material to the fibers of the filter, one provides protrusions that come into contact with the water that flows through openings 39. Note, the obstruction to normal flow through the filter is minimized since the material does not require a separate container nor is the material concentrated in one region of the filter system. That is, placement of a housing in the core of a filter creates a restriction in a narrowest portion of the system. In the present invention the bacteria killing material is placed in the portion of the system where the volume restriction is the least. That is, the area of the filter medium is large compared to the flow area through the core of the filter. Consequently, sufficient bacteria killing material can be dispersibly secured to the filter medium or proximate the filter medium so that the density of bacteria killing material per unit of flow area of the filter medium is small in comparison to the density of bacteria killing material which is required if the bacteria killing material is located in the core area of the filter. Thus, debris material which is larger than opening 39 is prevented from passing through the filer medium by the network of fibers while the water coming into contact with the bacteria killing material on the fibers receives the bacteria killing action. While only two layers of fibers are shown, it is apparent that multiple layers of fibers can be stacked to provide a torturous path for the water to follow thereby increasing the contact between the water and the bacteria killing material.

Figure 7A:
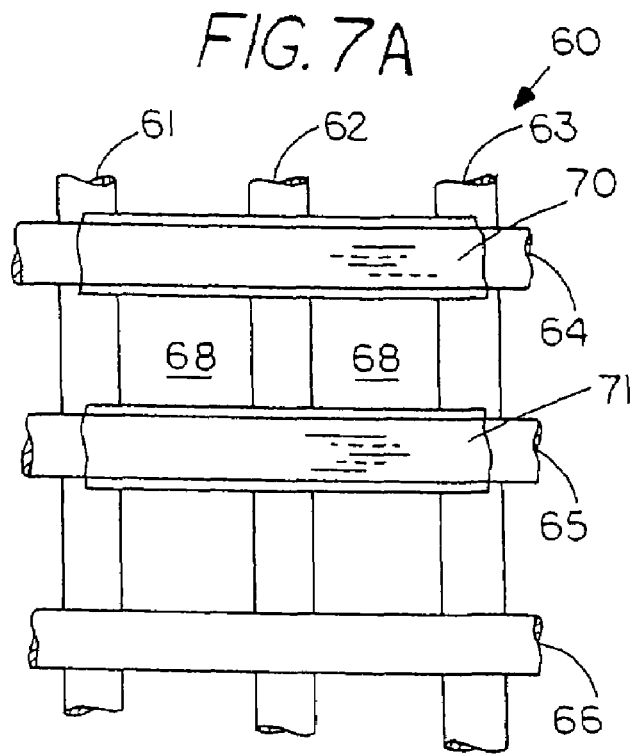
FIG. 7A is a front view of a portion of a filter medium having a purification material secured directly to the fibers by a thin film of non-water soluble porous adhesive.

FIG. 7A shows a portion of the filter medium 60 wherein the separate carrier for the water purification material such as a bacteria killing material has been dispensed with. In this preferred mode the portion of the filter medium includes fibrous members 61, 62 and 63 that intersect with members 64, 65 and 66 to form a plurality of openings 68 therethrough. In the embodiment shown the bacteria killing material is dispersibly secured directly to fibers by a thin film of non-water soluble porous adhesive 70 and 71. The adhesive 70 dispersibly secures the bacteria killing materials directly to the fibers of the filter medium in a condition to allow a controlled release of ions. In the embodiment shown, the bacteria killing material is preferably a controllable releasable ion yielding material selected from the group of metal ion yielding materials consisting of zinc sulfate, zinc carbonate, zinc chloride, copper carbonate, copper sulfate, silver chloride, stannous chloride and stannic chloride. Although an adhesive is described as a carrier for the water purification material the water purification can also be formed into film form and secured directly to the filter medium without the use of a separate carrier such as an adhesive.

Other ion yielding materials with controllable release include copper (II) acetate and its hydrates, copper (I) bromide and its hydrates, copper (II) bromide, copper (I) chloride and its hydrates, copper (II) chloride and its hydrates, copper (II) gluconate, copper (II) hydroxide, copper (II) oxide, copper sulfate, zinc acetate and its hydrates, zinc bromide and its hydrates, zinc carbonate hydroxide hydrate, zinc carbonate, zinc chloride and its hydrates, zinc citrate and its hydrates, zinc iodide and its hydrates, zinc nitrates and its hydrates, zinc oxide, zinc sulfate and its hydrates, silver acetate, silver carbonate, chelated silver ions, silver-exchanged zeolite, silver nitrate, silver oxide, silver sulfate, silver chloride, silver powder and colloidal silver, silver bromide and silver acetate.

In addition to water purification materials that kill bacteria, other water purification materials such as algaecides, clarifiers or even pH adjustment materials such as limestone can be carried by the present invention to provide the dual action of water screening for waste particles while simultaneously purifying the water.

Figure 8:
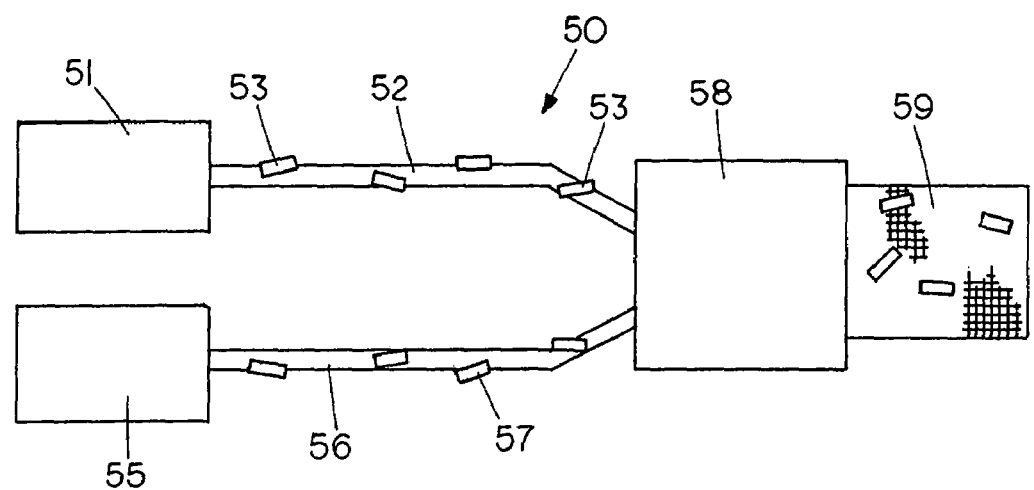
FIG. 8 is a partial schematic view of a system for manufacturing filter medium.
Figure 8A:
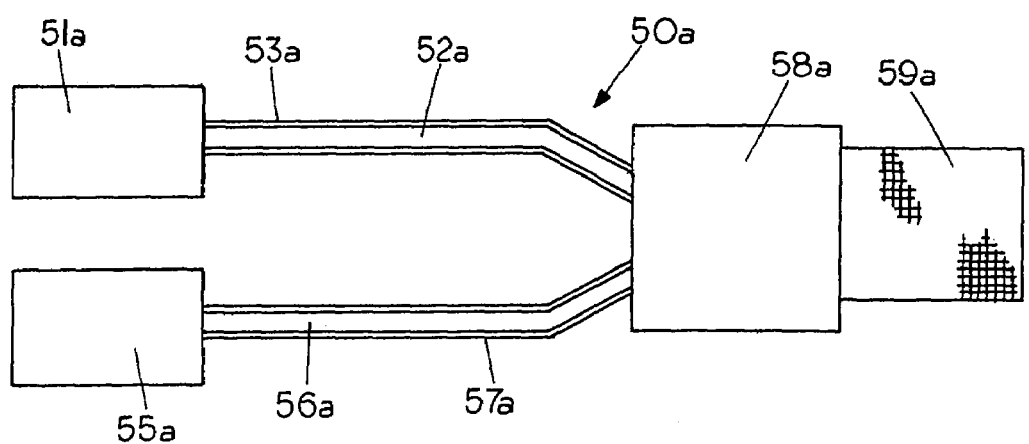
FIG. 8A is a partial schematic view of an alternative system for manufacturing a filter medium.

FIGS. 8 and 8A show methods of making a filter medium that can simultaneously filter out debris while purifying water with two different types of water purification material by placing the water purification materials on the fibers before weaving the fibers into a filter structure.

In the method illustrated in FIG. 8, the filter medium manufacturing system 50 includes a first station 51 for forming a fiber 52 having a plurality of a first bacteria killing materials such as zinc particles 53 secured thereto. A second station 55 includes a second fiber 56 having a second bacteria killing material such as silver chloride particles 57 secured thereto. The fibers are directed into a third station 58 that weaves the fibers into a porous filter medium 59 comprised of fibers with a first bacteria killing material thereon and fibers with a second bacteria killing material thereon which are located in proximity to each other to thereby provide the bacteria killing action from two different bacteria killing materials.

Although different embodiments are shown, in each embodiment the filter medium, which normally is used to remove debris from the water by screening the waste particles, is also used as a carrier for the first bacteria killing materials and the second bacteria killing materials which are dispersibly secured thereon so that water passing through the filter medium not only removes debris but also the bacteria is killed by the bacteria killing materials located on the filter medium.

In the method illustrated in FIG. 8A, the filter medium manufacturing system 50a includes a first station 51a for forming a fiber 52a having a film of a first bacteria killing material 53a secured thereto. A second station 55a includes a second fiber 56a having a film of a second bacteria killing material 57a secured thereto.

Similar to the method of FIG. 8, the fibers are then directed into a third station 58a that weaves the fibers into a porous filter medium 59a comprised of fibers with a film of a first bacteria killing material thereon and fibers with a film of a second bacteria killing material thereon which are located in proximity to each other to thereby provide the bacteria killing action from two different bacteria killing materials.

Also similar to the embodiment of FIG. 8, filter medium 59a of FIG. 8A is also used as a carrier for first bacteria killing material 53a and second bacteria killing material 57a which are secured thereon to provide a controlled release so that water passing through filter medium 59a not only removes debris removed but also the bacteria is killed by the bacteria killing materials located on filter medium 59a.

While bacteria killing materials are shown, other water purification materials such as algaecides, clarifier, etc . . . can be used. In addition the water purification materials can be embedded in the fibers rather than secured to the exterior of the fibers.

Figure 9:
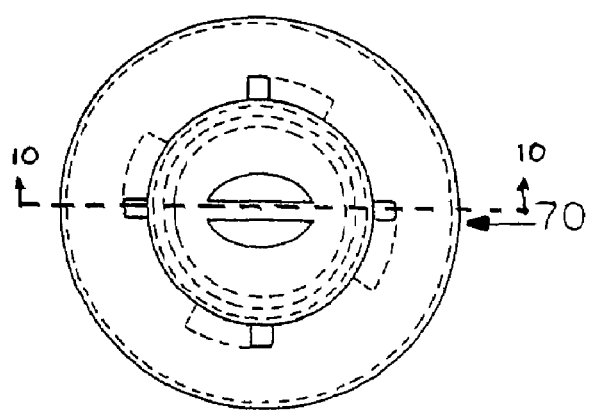
FIG. 9 is a top view a filter cartridge.
Figure 10:
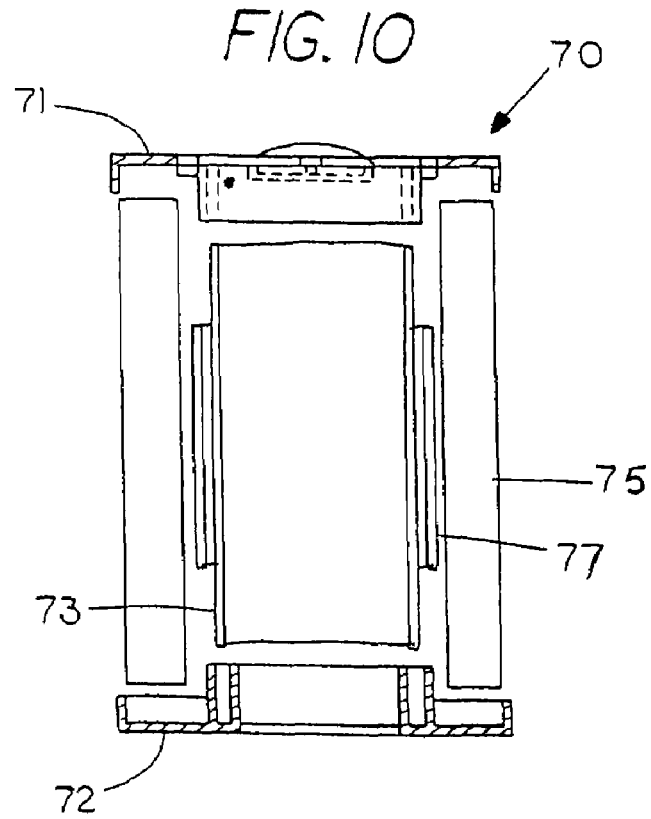
FIG. 10 is a sectional view taken along lines 10-10 of FIG. 9 to show the invention of a filter with a bacteria killing material located therein.

FIG. 9 is a top view a filter cartridge 70 and FIG. 10 is a sectional exploded view of filter cartridge 70 taken along lines 10-10. Filter cartridge 70 includes a top cap member 71 and a bottom cap member 72 with a rigid core tube 73 that connects top cap member 71 to bottom cap member 72. A filter medium 75, which is arranged in an annular shape with a series of pleats that extend circumferentially around the exterior of filter cartage 70. Located between core tube 73 is an annular carrier that is impregnated with a water purification material and more particularly to a bacteria killing material that controllably releases metal ions into water flowing through filter medium 75 to thereby effectively kill bacteria. In the present embodiment, carrier 77 can be form from either a rigid or flexible material. Thus the embodiment shown in FIG. 10 comprises a dual filter apparatus for water purification including water purification for potable water as well as for a swimming pool, hot tub or spa with the filter medium 75 comprising a network of openings therein to enable water to flow therethrough while retaining waste particles. The bacteria killing material, is dispersibly secured in an annular carrier insert 77 proximate the filter medium 75. The bacteria killing material is releasable over time so that the flow path of water through and around annular carrier insert 77 kills bacteria therein while the filter medium 75 removes waste particles to thereby enable the dual filter apparatus to simultaneously remove waste particles and kill bacteria. By having the insert 77 attached to the filter cartridge 70 one can simultaneously replace the bacteria killing material and the filter cartridge. However, if desired the insert could be separately replaceable. Although insert 77 is shown attached to filter cartridge it is envisioned that insert 77 could also be placed directly in the line leading to or away from the filter housing or on the inside of the filter housing and proximate the outside of the filter.

FIG. 10A is similar to FIG. 10 except that cartridge filter 70a is shown having an annular carrier insert 77a containing purification material engaging the exterior surface of the rigid core tube 73 of filter cartridge 70a. In the present embodiment, annular carrier insert 77a may be made from an elastic or flexible material with the water purification material held thereon through adhesion or physical containment thereof.

In the operation of the filter medium of FIGS. 10 and 10A, water flows through the openings of filter medium 75 while the debris particles present in the water encounter the external network of filter medium 75 where they are screened off and prevented from flowing through filter medium 75. In FIG. 10, after the water is filtered by filter medium 75, the water then engages annular sleeve 77 where purification materials present in the sleeves are released to purify the water. In FIG. 10A, after the water is filtered by filter medium 75, the water then engages annular sleeves 77a where purification materials present in the sleeves are released to purify the water. One way of purifying the water would be by releasing materials that kill bacterial and viral agents that are present in the filtered water.

FIG. 10B is a view similar to FIG. 10 except that a cartridge filter 70b is shown having an annular carrier 77b carrying a water purification material with the carrier engaging the exterior surface of the filter cartridge 70b. Exterior placement of carrier 77b allows one to replace the carrier and spent water purification materials without replacing the filter cartridge.

In the operation of the filter cartridge of FIG. 10B, water flows through the openings of annular carrier insert 77b while large debris particles present in the water encounter the external network of annular carrier insert 77b where they are screened off and prevented from flowing through the annular carrier insert. For example, as water flows through the annular carrier insert 77b, various water purification materials present within insert 77b are released to kill bacterial and viral agents that are present in the water. Once the water passes through insert 77b, the water is then filtered by filter medium 75 before the water enters into core 73. The filter medium 75 is capable of screening out smaller debris particle that were able to pass through the network of annular carrier insert 77b.

Figure 11:
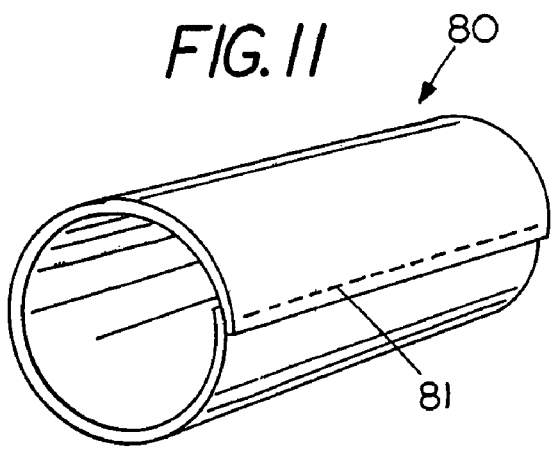
FIG. 11 is a perspective view of a filter sleeve that has been formed from a single piece of cloth with the filter stitched and sonic welded into an annular shape.
Figure 11A:
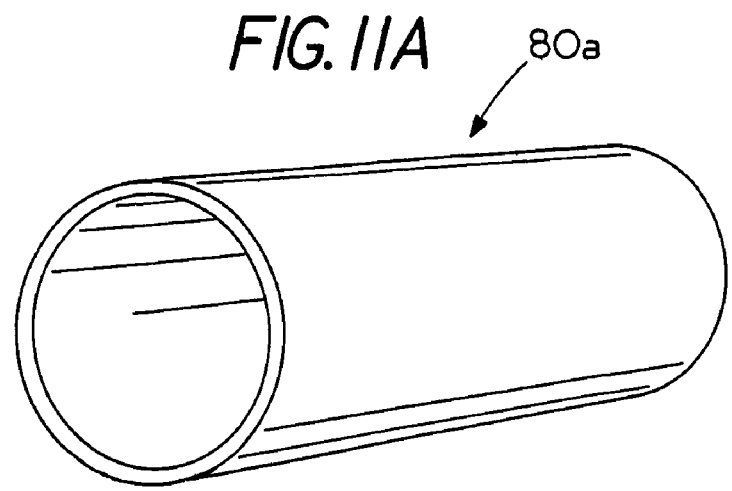
FIG. 11A is a perspective view of a porous annular filter sleeve.

FIGS. 11 and 11A are perspective views of a porous annular filter sleeve, the sleeves containing a water purification material. FIG. 11 shows a porous filter sleeve 80 that has been formed from a single piece of flexible material with the material containing a sonic weld 81 that holds the material in an annular shape. The single piece of material can form an external sleeve for dispersibly carrying the bacteria killing material. That is, the sleeve 80 includes a porous material that screens out debris while letting water through with a bacteria killing material dispersibly secured thereto. The bacteria killing material is controllable releasable as water flows through the filter sleeve.

FIG. 11A shows a one-piece porous annular filter sleeve 80a that can either be formed from a rigid material or formed from elastic or flexible material. Similar to filter sleeve 80, annular filter sleeve 80a includes a porous material that screens out debris while allowing water through. It should be pointed out that the screening performed by the sleeve 80a is a secondary screening in that the primary screening is performed by the filter cartridge that supports the filter sleeve. In the embodiment shown filter sleeve 80a contains a water purification material such as a bacteria killing material dispersibly secured thereto and is controllably releasable as water flows through the filter sleeve.

Figure 22:
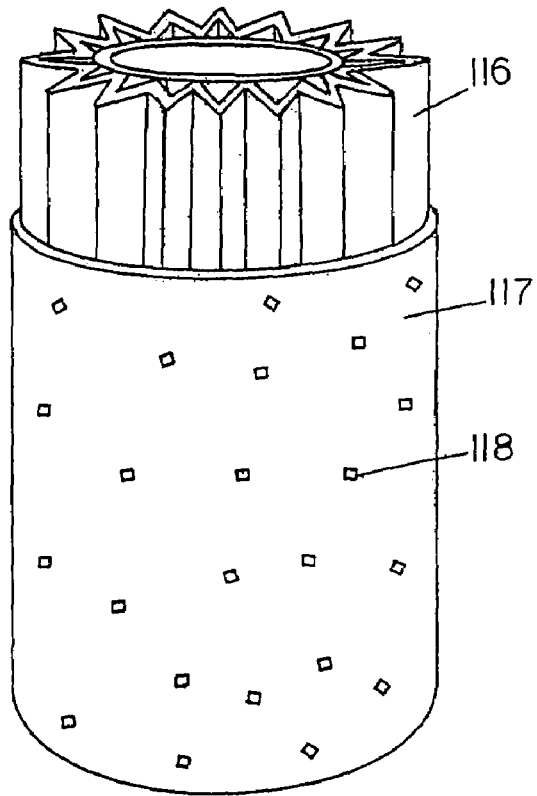
FIG. 22 is a pictorial exploded view showing a filter medium having an annular sleeve engaging the exterior surface of the filter medium.

When formed from a sheet of elastic or flexible material, filter sleeve 80a can be placed around a filter cartridge such as shown in FIG. 10B, around a filter medium as shown in FIG. 22, or around a filter cartridge core as shown in FIG. 10A, to provide in situ release of water purification material.

In operation, filter sleeves 80 and 80a can be placed on the outside of a filter cartridge to release water purification materials such as bacteria killing materials to water flowing through the filter cartridge. By placing the proper size sleeve on the cartridge a user can on an after market basis match the life of the filter medium as a screener of waste particles to the amount of bacteria killing material necessary to kill bacteria during the useful life of the filter so that the filter can simultaneously screen waste particles and kill bacteria to provide a dual water filter apparatus.

If desired the sleeve can be spaced from the filter medium so as to permit exchange of the filter medium without removing the sleeve with the water purification. Also the water purification material can be applied to an inner surface of housing of the cartridge or a sleeve to permit one to achieve independence between the life of the water purifier and the live of the filter medium.

Figure 12:
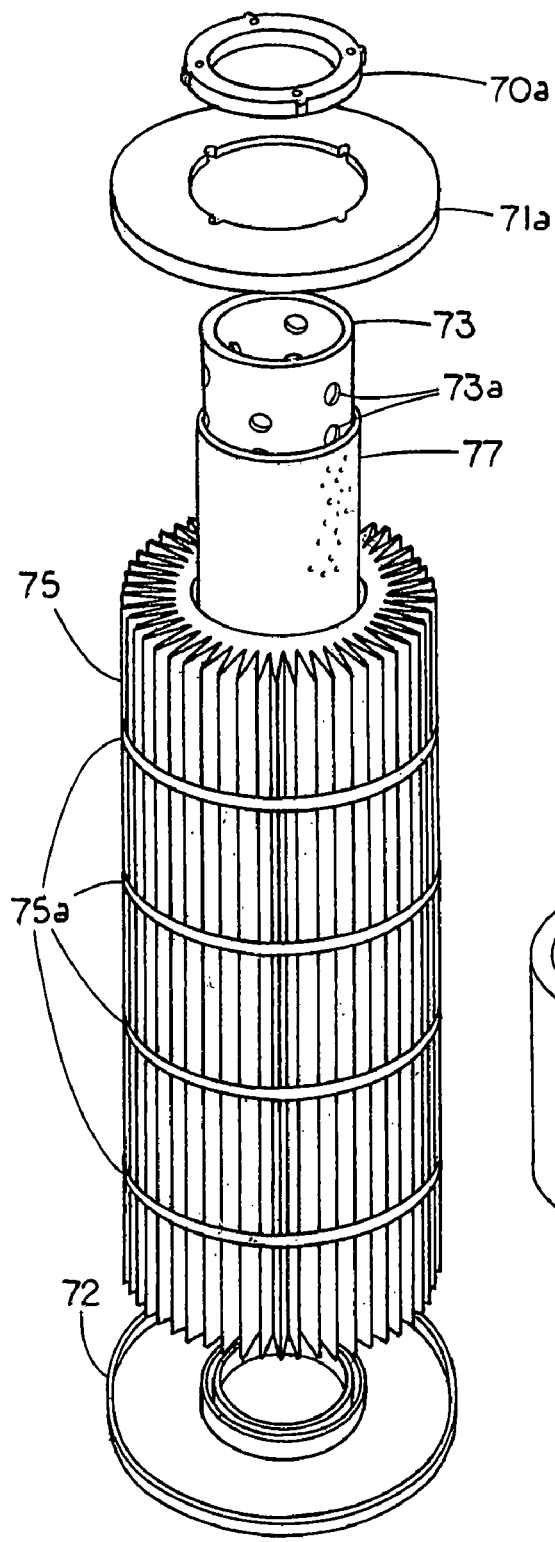
FIG. 12 is an exploded pictorial view of a filter cartridge housing contain a bacteria-killing material.

FIG. 12 is a pictorial exploded view of filter cartridge 70 showing the filter core tube 73 with openings 73 therein for flow of water therethrough. Positioned next to core tube 73 is annular porous sleeve 77 that carries a water purification material dispersed therein that becomes an integral part of the filter. That is annular sleeve 77 sits between core tube 73 and annular filter medium 75. A set of bands 75a is located in a spaced condition around the periphery of filter medium 75 to maintain the integrity of the filter medium.

Figure 13:
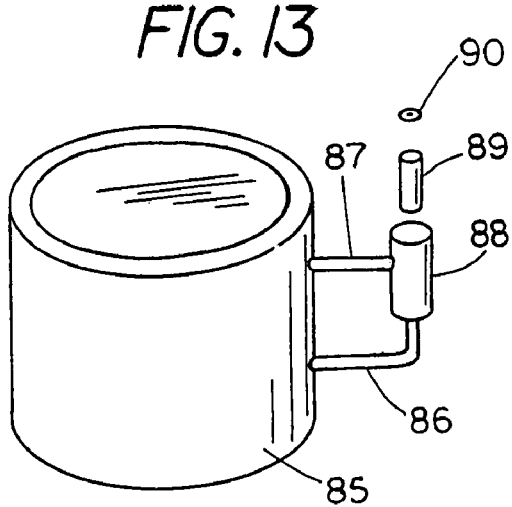
FIG. 13 is partial schematic view of a dual filter system for simultaneously removing debris and killing bacteria.

FIG. 13 is a partial schematic view of a system for water purification wherein debris and bacteria are simultaneously removed by a replaceable cartridge. The water purification system includes a container 85 for holding water to be purified. An outlet 86 directs water to filter housing 88 wherein a cartridge filter 89 having a filter medium with a bacteria killing material secured thereto is located. A cap 90 is placed onto top of container 88 to hold filter cartridge 89 therein. The water circulates back into container 85 through conduit 87. Thus it can be envisioned that the system is suitable for water purification of potable water as well as swimming pools, hot tubs or spas, which need to maintain the water free of debris as well as free of harmful bacteria.

While the ion yielding material is shown mechanical secured to the filter medium or an insert through an adhesive it is envisioned that in certain types of filters the ion yielding materials could be integrally formed into a portion of a filter medium or a water cartridge housing such as an end cap or the filter core. Thus it is envisioned that the water purification material which is yieldable in the presence of water can be carried either within a porous structure of the housing or a porous structure of the filter medium or dispersibly secured to the filter medium so that the water purification material can be released as water contacts the housing.

Thus in one embodiment of the invention the invention comprises a water filter structure that minimizes obstruction to normal flow through the filter housing. The housing including at least a portion therein containing a water treatment composition that yields a water treatment composition material in the presence of water. A filter medium secured to the cartridge has a network of openings sufficiently large to allow water to flow therethrough but sufficiently small to prevent waste particles from flowing therethrough so that when water flows through the housing the water treatment composition performs an action to the water while the filter medium screens out waste particles from the water. Examples of water treatment compositions that perform an action include algaecides, bactericide, clarifiers, pH adjusters (for example, limestone) and foam suppressants.

FIG. 14 show a partial cross-sectional view of water filter cartridge 91 and FIG. 15 show a partial cross-sectional view of water filter cartridge 91a. Each of the cartridges is shown having a top cap member 92, a bottom cap member 93, a filter medium 95a, water filter cartridge core 94. Filter cartridge 91 has a water purification material carrier 96 located within the water filter cartridge core 94 for the time controlled releasing of water purification material into the water. Similarly, filter cartridge 91a has a water purification material carrier 97 located within the water filter cartridge core 94 for the time controlled releasing of water purification material into the water.

The water purification material carrier 96 of FIG. 14 comprises a non-woven fibrous material located within water filter cartridge core 94 of filter cartridge 91. The fibrous material can be made from a variety of materials including rubber, plastic and metal. The fibrous material can be coated with a water purification material or the water purification material can be impregnated into the fibrous material.

The water purification material carrier 97 of FIG. 15 is located within water filter cartridge core 94 of the filter cartridge 91a and comprises water purification materials 97b, which are located either on carrier 97 or within an interior of an annular sleeve 97a. Carrier 97 can be made from various materials such as plastic, or metal and includes openings or pores therein to permit water to contact the purification material. If desired openings 97c can be provided for ingress and egress of water through carrier 97. The openings should be sufficiently small to retain the water purification material therein when it is in a ready to use condition.

Purification material carriers 96 and 97 can either be permanently installed within water filter cartridge core 94 so as to be replaceable with the filter medium 95 or are separately replaceable once their purification material has been depleted.

In the replaceable form, the steps for the replacement of the water purification material comprises (1) removing the top cap member 92 or bottom cap member 93 from the filter cartridge 91; (2) removing the depleted water purification material from water filter cartridge core 94; (3) inserting a fresh water purification material within the filter cartridge core 94; and (4) attaching the cap member back on the filter cartridge 91.

In normal operation of the filter cartridges of FIGS. 14 and 15, filter cartridge 91, 91a allow for the flow of water through the openings of filter medium 95 while simultaneously preventing debris particles present in the water from flowing therethrough. Once through filter medium 95, the filtered water flows into the filter cartridge core 94 where the water engages the water purification material carrier to thereby release the water purification materials. For example, one purifies the water by killing contaminates such as bacteria, viruses, and algae that are present in the filtered water.

Figure 16:
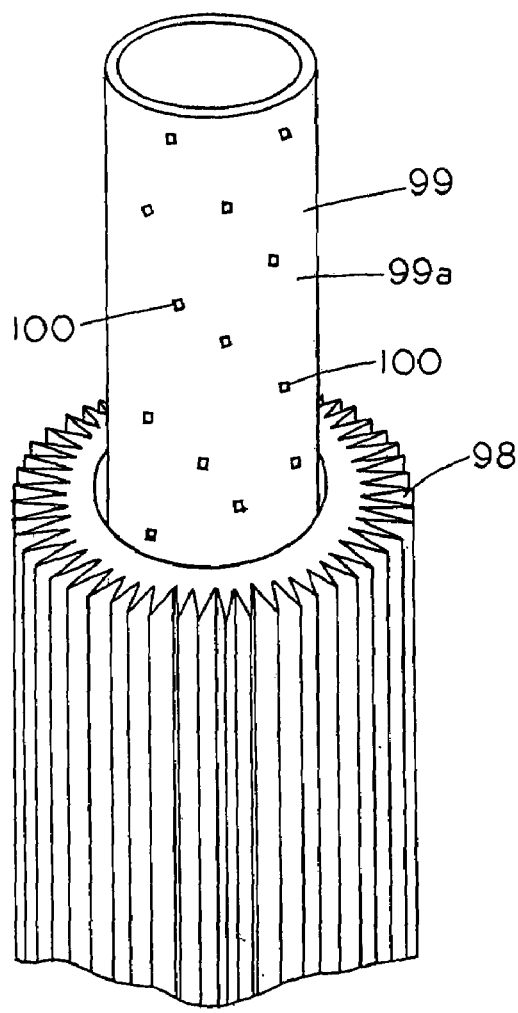
FIG. 16 is a pictorial exploded view of a filter medium having a hollow core containing a purification material and located within the interior of the filter medium.
Figure 17:
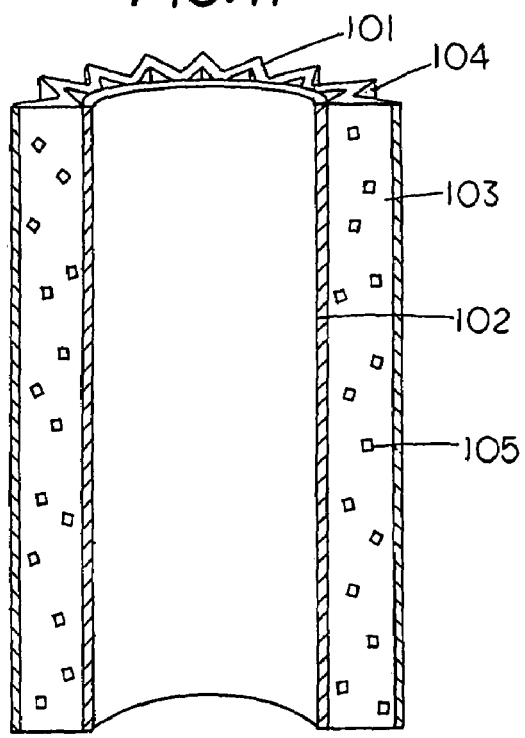
FIG. 17 is a partial cross-sectional view of a filter medium having a purification material located within the interior of the filter medium.

FIG. 16 is a pictorial exploded view of a filter medium 98 having a hollow water porous core 99 located within the interior of filter medium 98 and containing at least one water purification material 100 dispensed thereon. In the present embodiment, the hollow core 99 can be made from a variety of materials including rubber, plastic and metal. After water porous core 99 is formed, water purification material 100 is then coated onto the surface 99a of the filter water porous core 99. Alternatively, water porous core 99 may also be formed from an adhesive mixed with or containing the water purification material 100. Although the core is described as water porous it is envisioned that the core need not be water porous if the normal circulation of water through the filter is not curtailed. For example, a core 99 having a length less than the length of the cartridge filter medium would allow normal as water could flow past the core carrier without having to flow thorough the core carrier FIG. 17 shows a partial cross-sectional view of a pleated filter medium 101 having a hollow porous core 102 located within an interior of the filter medium 101. As shown in FIG. 17, pleated filter medium 101 has an interior surface 103 with purification materials 105 such as a bactericide like silver chloride dispersibly secured thereto for purifying water that enters through filter member 101.

Figure 18:
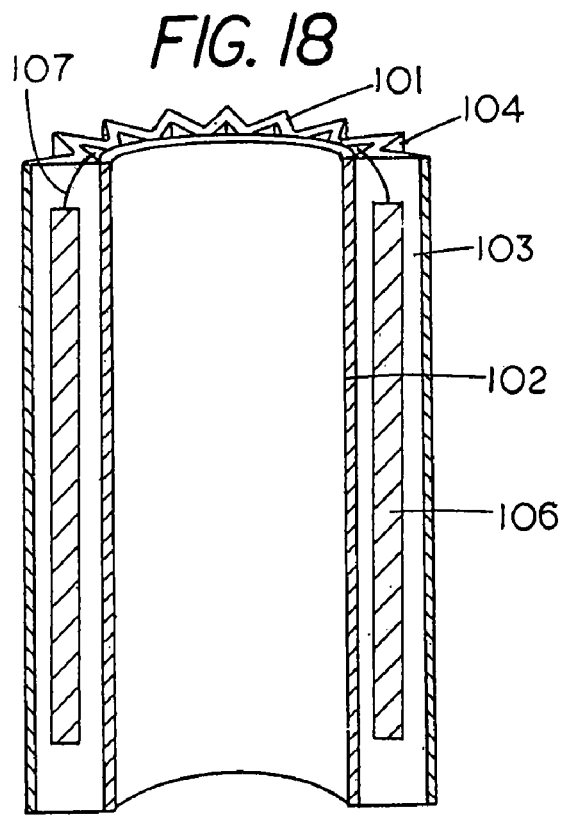
FIG. 18 shows a partial cross-sectional view of a filter medium having a plurality of elongated members containing water purification materials secured to the interior surface of the filter medium.

FIG. 18 is similar to FIG. 17 except that the purification material is secured to the interior surface 103 of pleated filter medium 101 in the form of an elongated member 106. Although FIG. 18 shows elongated member 106 held proximate to the interior surface 103 of the pleated filter medium 101 by a wire hook 107, elongated member 106 can also be secured to filter medium 101 in alternative ways such as by a stitching, and by an adhesive.

In the operation of the filter medium of FIG. 17 and FIG. 18, water flows through the openings of pleated filter medium 101 while debris particles present in the water encounter the external network of the filter medium 101 where they are screened off and prevented from flowing through filter medium 101. As water flows through the filter medium of FIG. 17, purification materials 105, located on the interior surface 103 of filter medium 101, are released to purify the water. Similarly, as water flows through the filter medium of FIG. 18, the water purification material 106 is released. Releasing a material for killing of bacterial and viral agents that are present in the filtered water allows one to both purify the water and remove debris from the water. It should be understood that filter cartridges can be used for screening debris by flow in either flow direction i.e. radial inward flow or radial outward flow. In order to minimize the effect of debris on the water purification materials the water purification materials can be placed on the downstream side of the filtering section so that the filtered water is purified rather than the non-filtered water.

Figure 18A:
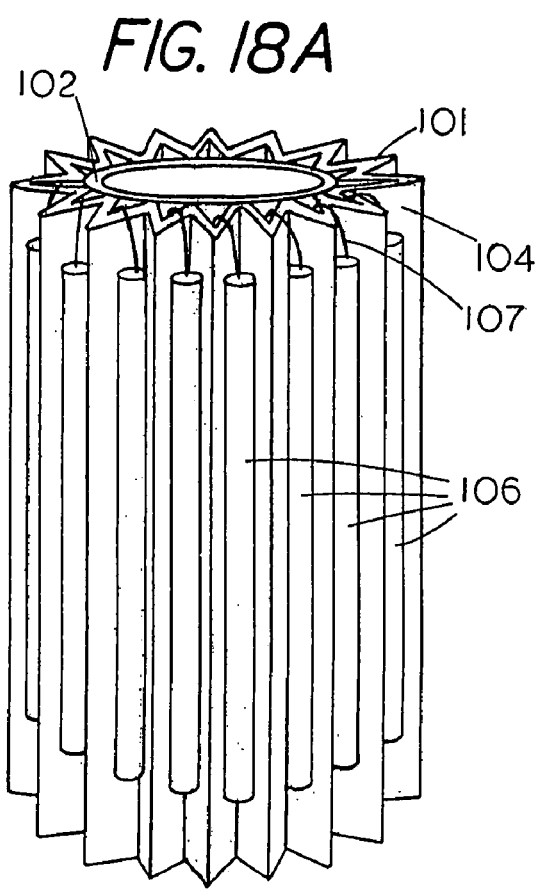
FIG. 18A shows a perspective of a pleated filter medium having a plurality of elongated members containing water purification materials secured to the exterior surface of the filter medium.

FIG. 18A shows a perspective view of pleated filter medium 101 having a plurality of cylindrical elongated members 106 containing water purification materials. The members are held proximate to the exterior surface 104 of the pleated filter medium 101 by a wire hook 107. Similar to FIG. 18, although elongated member 106 is shown held proximate to the exterior surface 104 of pleated filter medium 101 by wire hook 107, elongated member 106 can also be secured to the filter medium 101 in other ways including by a stitching, and by an adhesive.

Although FIG. 18A shows the use of a plurality of elongated members secured between the pleats of the filter medium 101, the number of elongated members that are secured to the filter medium 101 may vary from as little as one elongated member to a plurality of elongated members, depending on the user's needs. When more than one elongated member is secured to the filter medium 101, each elongated member may contain the same purification material 101, or a different purification material, depending on the user's needs and desires.

In embodiments in which there are more than one adjustable water purification material dispensers, chamber 109 of the purification material dispensers 108 may either carry the same water purification material or different types of water purification materials from each other or the combination of different purification material, again, depending on the user's needs. For example, the adjustable water purification material dispensers of the present embodiment may both carry the same water purification material such as silver chloride or one may carry silver chloride while the other carry a different water purification material such as an algaecide.

Figure 19A:
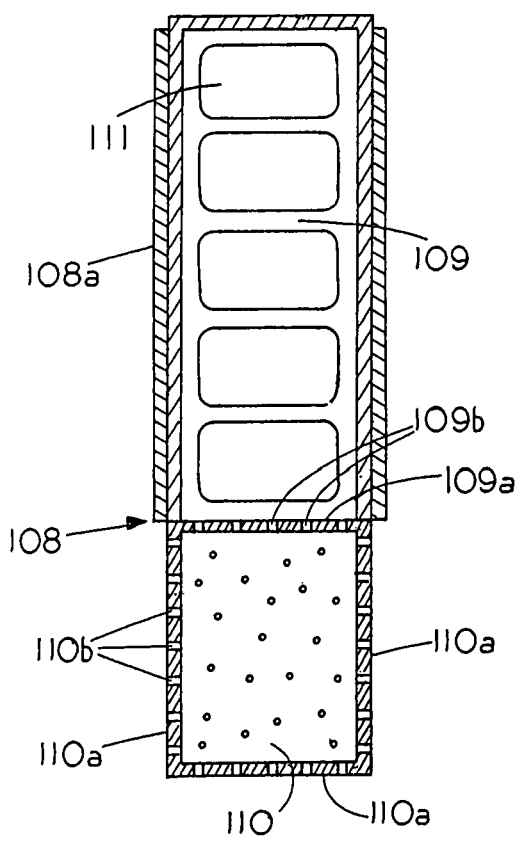
FIG. 19A shows a close-up view of the adjustable water purification material dispenser.

FIG. 19A is a close-up view of adjustable water purification material dispenser. Purification material dispenser 108 includes a chamber 109 for storing purification materials 111. Chamber 109 of the present dispenser is sufficiently flexible so as to be able to support water purification materials of various shapes and sizes including water purification materials form in the shape of pellets, sticks, and strips. Purification material dispenser 108 also includes a second chamber 110 for the time controlled releasing of purification materials 111. As shown in FIG. 19A, a plurality of openings 109b in divider 109a permit ingress and egress of water into chamber 109. Also a plurality of outlet walls 110a containing a plurality of openings 110b allowing for the flow of water therethrough. Thus in the embodiments shown in FIG. 19a two separate compartments are provided for two different water unification materials with fluid ingress and egress permitted to both compartments. Located on an exterior surface of purification material dispenser 108 is a slideable sleeve 108a for selectively blocking off water flow through outlet openings 110b. Sleeve 108 is used to control the amount of water that enters purification material dispenser 108 thereby controlling the amount of water purification material that purification material dispenser 108 releases.

In the operation of dispenser 108, water first enters outlet 110 by flowing through the outlet openings 110b of outlet walls 110a that are not cover by sleeve 108a. Water then enters chamber 109 through openings 109b of divider 109a and interacts with purification materials 111. The interaction between the water and purification material 111 allows a portion of purification material 111 to be released into the water. After a portion of purification material 111 has been released into the water, the purification material is then carried by the water out of chamber 109 through openings 109b of divider 109a and out of outlet 110 by way of outlet openings 110b. To control the amount of water purification material that is release by dispenser 108, a user simply slides sleeve 108a to cover more or to cover less outlet openings 110b of outlet walls 110a, thereby controlling the amount of water flowing into and out of dispenser 108.

Figure 19B:
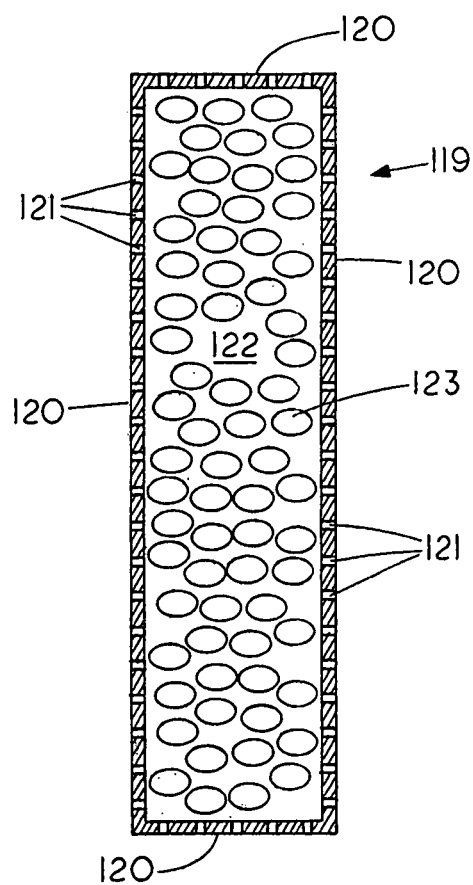
FIG. 19B shows an alternative embodiment of a water purification material dispenser.

FIG. 19B shows a partial cross-sectional view of an alternative water purification material dispenser 119. Purification material dispenser 119 is defined by a plurality of walls 120, each of the walls 120 having a plurality of openings 121 allowing for the flow of water therethrough. Located within purification material dispenser 119 is a water purification material supporting chamber 122 for holding a water purification material 123, the water purification materials being larger than the openings to retain the undissolved water purification material therein. As water flows through the chamber the water purification materials are released to purify the water.

In the operation of purification material dispenser 119, water passes into chamber 122 by way of openings 121. Once in chamber 122, the water interacts with purification material 123. The interaction between the water and the purification material 111 allows a portion of purification material 123 to be released into the water. After a portion of purification material 123 has been released into the water, the water then carries the purification material out of chamber 122 through plurality of openings 121.

Figure 20:
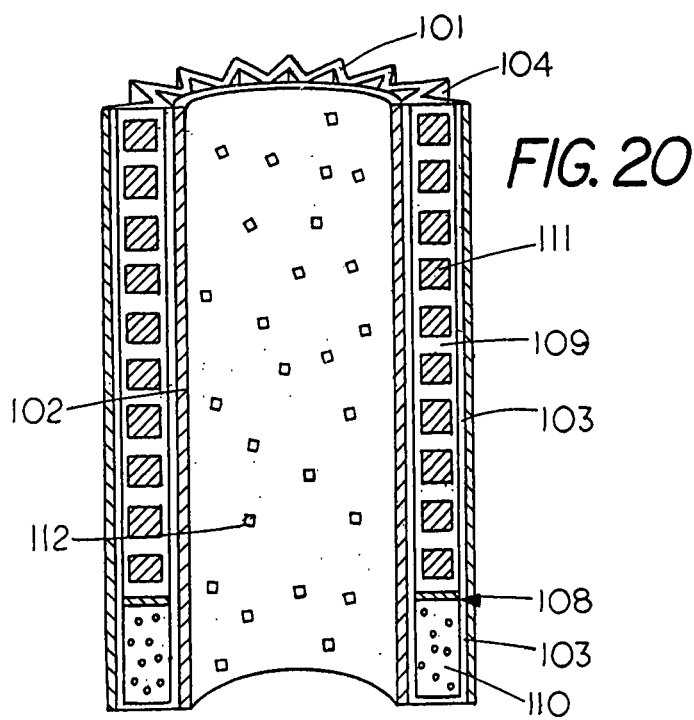
FIG. 20 shows filter medium having a dispenser secured to the interior surface of the filter medium and the cartridge core coated with a water purification material.

Figure shows the hollow water porous core 102 coated with water purification material 112. In FIG. 20, the water purification material 112 coated on core 102 may either be the same as the water purification materials 111 that are located in the chamber 109 of the adjustable water purification material dispensers 108 or alternatively, may be of a different water purification material.

In the operation of the embodiment of FIG. 20, water flows through the openings of the exterior surface 104 of pleated filter medium 101 while the debris particles present in the water encounter the external network of the filter medium 101 where they are screened off and prevented from flowing through the filter medium 101. As water flows through the interior surface 103 of filter medium 101, the water encounters the adjustable water purification material dispensers 108. Purification materials 111 present within chamber 109 of dispensers 108 move to outlet 110 where they are then released to purify the water.

In the embodiment of FIG. 20, after the water has been purified by water purification material 111, the water then moves through filter medium 101 to reach the water porous core 102 where a second water purification material 112, located on the core 102, is dispensed to further purify the water as the water flows through openings in the core.

Figure 21:
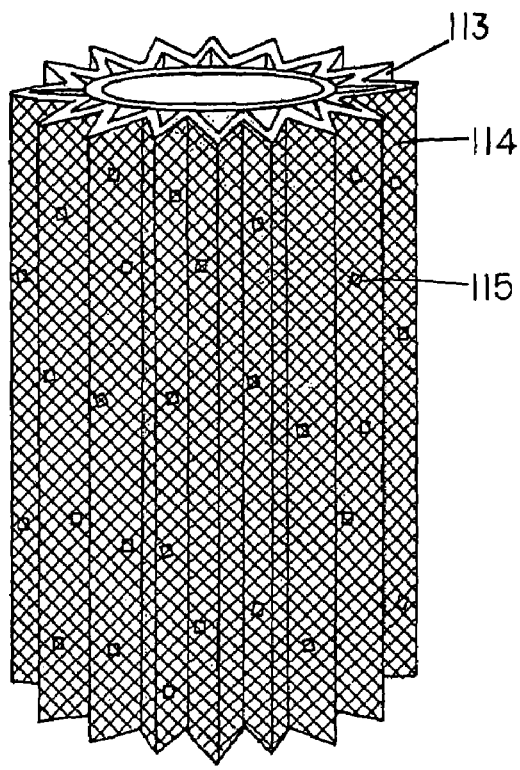
FIG. 21 shows a mesh screen coated with purification materials engaging the exterior surface of a filter medium.

FIG. 21 shows a mesh screen 114 coated with a water purification material 115 and engaging the exterior of a filter medium 113. The mesh screen 114 can be made from a variety of materials including plastic and metal.

Mesh screen 114 contains a plurality of openings for screening waste particles of larger size from the water. In normal operation of mesh screen 114, large debris particles encounter the external network of mesh screen 114 where they are screened out while water is allowed to flow therethrough. As water flows through mesh screen 114, the water purification materials 115 are time controllably released from the mesh screen to purify the water, such as by killing bacterial and viral organisms. The water is then further screened of debris by flowing through the filter medium 113, which prevents the smaller debris that were able to flow through the network of the mesh screen from flowing through filter medium 113. Since filter medium 113 only has the job of screening out the smaller debris particles present in the water, the use of the screen mesh can extend the life of filter medium 113.

FIG. 22 is a pictorial exploded view showing a filter medium 116 having an annular water porous sleeve 117 containing a water purification material 118 engaging the exterior surface of the filter medium 116. Although annular sleeve 117 may be of a rigid material, it is preferred that the annular water porous sleeve of the present embodiment be made of an elastic or flexible material.

The method of operation of the for the embodiment of FIG. 22 is very similar to the method of operation for the embodiment of FIG. 21 in that water and smaller debris particles are allowed to flow through the openings of annular sleeve 117 while larger debris particles encounter the external network of sleeve 117 where they are prevented from flowing therethrough. As water flows through sleeve 117, water purification materials 118 are time controllably released to purify the water. The purified water is then further filtered of debris by flowing through the filter medium 116, which prevents the smaller debris that were able to flow through sleeve 117 from flowing through the filter medium 116. Since the filter medium 116 only has to screen the smaller debris, the use of the annular water porous sleeve 117 will extend the life of the filter medium 116 as well as purify the water.

Depending on the size of the openings for annular sleeve 117, annular sleeve 117 may alternatively be used as an ultra-purification system in which the openings of annular sleeve 117 may be sufficiently small to not only screen out the larger debris but also the smaller debris. Once screened by annular sleeve 117, the water would then be screened for a second time by filter medium 116 to remove small debris that was missed by the annular sleeve 117.

While the present invention has been described in relation to water treatment materials the present invention is also suitable for other fluid activators while performing the debris screening process. By activators it is meant to include other materials that are added to a fluid to change some characteristic of the fluid and could include for example chemicals or the like that react with foreign particles in the fluid to render the foreign particles harmless. A feature of the present invention when used with activators that kill organisms that grow on the filter is that the life of the filter is extended by avoiding the build up of bacteria or other organisms on the filter which would normally accumulate and shorten the life of the filter. Thus, with the present invention one can produce a multiple purpose filter medium for screening out debris particles, with the filter medium having an exterior surface and an interior surface; and an activator, which could be liquid or solid or both that can be retained by the filter medium to thereby allow the filter medium to in situ screen out debris while at the same time the activator acts on the fluid that flows through the filter medium.

While the activator or water purification material can be held on the surface of the filter medium in some applications it may be desirous to maintain the purification material within the pores of the filter medium.

As an alternate method of securing the water treatment material or activators in the fluid stream one can apply the activator as one would apply paint to a surface. This procedure of stroking or spraying the activator on a surface allows one to on-site refurbish a filter that may be spent. This procedure eliminates the need for a separate carrier for the water purification materials as.

I claim:

1. A method of making a dual filter for in situ water purification that minimizes obstruction to normal flow through a filter housing comprising:

weaving a first fiber with a second fiber to form a porous water filter medium, said porous water filter medium allowing water therethrough but preventing waste particles from flowing therethrough; and securing a controllable release water purification material to said water filter medium to enable said water filter medium to simultaneously screen waste particles from a water source and purify water that come into contact with said water purification material.

2. The method of claim 1 wherein the step of securing the releasable water purification material comprises securing a first releasable water purification material to the first fiber and securing a second releasable water purification material to the second fiber.

3. The method of claim 2 wherein the steps of securing the first water purification material to the first fiber and securing the second water purification material to the second fiber comprises dispersibly securing the first water purification material to the first fiber and dispersibly securing the second water purification material to the second fiber.

4. The method of claim 2 wherein the steps of securing the first water purification material to the first fiber and securing the second water purification material to the second fiber comprises securing a film of the first water purification material to the first fiber and securing a film of the second water purification material to the second fiber.

5. The method of claim 2 wherein the steps of securing the first water purification material to the first fiber and securing the second water purification material to the second fiber comprises securing a first bacteria killing material to the first fiber and securing a second bacteria killing material to the second fiber.

6. The method of claim 5 wherein the steps of securing a first bacteria killing material to the first fiber and securing a second bacteria killing material to the second fiber comprises securing a first metal ion yielding material to the first fiber and securing a second metal ion yielding material to the second fiber.

* * * * *